United States Patent
Hartman et al.

(10) Patent No.: US 12,176,083 B2
(45) Date of Patent: Dec. 24, 2024

(54) AUTOMATED SUMMARIZATION OF A HOSPITAL STAY USING MACHINE LEARNING

(71) Applicant: Abstractive Health, Inc., New York, NY (US)

(72) Inventors: Vincent Christopher Hartman, New York, NY (US); Sanika Bapat, Boston, MA (US)

(73) Assignee: Abstractive Health, Inc., New York, NY (US)

( * ) Notice: Subject to any disclaimer, the term of this patent is extended or adjusted under 35 U.S.C. 154(b) by 246 days.

(21) Appl. No.: 17/885,714

(22) Filed: Aug. 11, 2022

(65) Prior Publication Data

US 2023/0081372 A1 Mar. 16, 2023

Related U.S. Application Data

(60) Provisional application No. 63/241,903, filed on Sep. 8, 2021.

(51) Int. Cl.
| | |
|---|---|
| *G16H 15/00* | (2018.01) |
| *G06F 40/40* | (2020.01) |
| *G16H 10/60* | (2018.01) |
| *G16H 50/20* | (2018.01) |

(52) U.S. Cl.
CPC .............. *G16H 15/00* (2018.01); *G06F 40/40* (2020.01); *G16H 10/60* (2018.01); *G16H 50/20* (2018.01)

(58) Field of Classification Search
CPC ........ G16H 15/00; G16H 10/60; G16H 50/20; G06F 40/40; G06F 40/279; G06F 16/345
See application file for complete search history.

(56) References Cited

U.S. PATENT DOCUMENTS

| | | | | |
|---|---|---|---|---|
| 2013/0103389 A1* | 4/2013 | Gattani | ................ | G06F 40/295 704/9 |
| 2015/0163184 A1* | 6/2015 | Kanter | .................... | H04L 51/52 709/204 |
| 2018/0301152 A1* | 10/2018 | Montyne | ................ | G16H 15/00 |
| 2020/0258628 A1* | 8/2020 | Zalis | ...................... | G16H 40/20 |
| 2021/0216200 A1* | 7/2021 | Strader | ................... | G06F 40/30 |

* cited by examiner

Primary Examiner — Eliza A Lam
(74) Attorney, Agent, or Firm — Soquel Group LLC

(57) ABSTRACT

A method and a device are provided for generating a summary of a hospital stay by a patient, including maintaining a database of electronic medical records (EMRs) where the EMRs include clinical notes pertaining to a patient during a time interval, identifying a set of significant physician notes for the time interval, generating a candidate set of summaries for each of the significant physician notes, for each significant physician note, analyzing the factuality of each of the candidate summaries and selecting the most factual summary, and generating a daily section for inclusion in a hospital course section of a discharge note that includes the selected factual summary for each of the significant physician notes.

22 Claims, 6 Drawing Sheets

Example Discharge Summary 100

Discharge Summary

Admission Date: 08/01/2020

Discharge Date: 08/04/2020

Date of Birth: 04/05/1962

Sex: Female

Principal Diagnosis: Pneumonia

Hospital Course Section:
58 year old, Spanish speaking, female with a past medical history of hypertension. She presented to the emergency department with complaints of fever, chills, night sweats, shortness of breath, and cough productive of brownish sputum for the past three days. The patient was admitted on 8/1 for right middle lobe pneumonia as well as renal insufficiency. The patient was started on Levaquin on 8/2. Blood cultures were done. The patient had urine toxicology, which came out to be positive for methadone with drug screen and opiates on 8/3. The patient's ABG was 7.46, 33, and 17.6. The patient was subsequently discharged on 8/4 to home.

Follow-ups:
- Return to your PCP in 2 weeks.
- Levaquin with plan to follow up in medical clinic.
- You will need a cat scan.

Medications at Admission: Benadryl, Trazadone 50 mg, Aspirin 20 mg, Vitamin E 500mg

Discharge Medications: Zolpidem 5 mg, Trazadone 50 mg, Acetaminophen 500mg, Azithromycin 10mg

FIG. 1

AUTOMATED SUMMARIZATION OF A HOSPITAL STAY USING MACHINE LEARNING

TECHNICAL FIELD

Various embodiments generally relate to a method using deep learning that automates the creation of certain sections of hospital records, in particular the hospital course section of the discharge summary.

BACKGROUND

Various studies have investigated methods for automatically creating patient summaries using electronic health record (EHR) content. This would have the benefits of reducing the time that a physician spends using a computer, thus reducing costs and freeing up time to treat patients.

Natural Language Processing (NLP) can be used to automate the creation of EHR content. An example of EHR content is the discharge summary, which is a document used to communicate clinical information to outpatient providers at the conclusion of an inpatient stay. A streamlined example of a discharge summary is given in FIG. 1. In addition to the hospital course section, the discharge summary contains other elements including but not limited to the principal diagnosis, the past medical and social history, allergies, medications, follow-up plans and laboratory data.

Physicians currently write a narrative summary within the inpatient discharge summary known as the hospital course section. The hospital course section serves as the primary summary for communicating what happened to the patient during their inpatient stay. Automating creation of the hospital course section would have the benefits of saving physicians' time as compared to the current approach of summarizing Electronic Medical Record (EMR) content manually, improving speed and accuracy in preparing discharge, and the hospital course section would be more concise. Automating the creation of the hospital course section is challenging as the narrative is composed from a large corpus of clinical data. For this reason, no adequate approaches currently exist for automating the hospital course section.

Abstractive text summarization, or abstractive summarization, has been proposed as a means to alleviate clinical documentation burden by summarizing, i.e. condensing, clinical notes. Abstractive text summarization is the task of generating a short summary consisting of a few sentences that captures the salient ideas of a note, article or a passage. The term 'abstractive' denotes a summary that is simply a selection of a few sentences in the source document, but is, rather, a compressed paraphrasing of the main contents of the document.

A current limitation of abstractive summarization is that while models can produce highly fluent narratives, they can often produce inconsistent statements that are not supported by the original source text; this is particularly problematic when summarizing summaries of clinical notes.

Encoder-decoder transformer models can generate fluent summaries with state-of-the-art performance and condense the underlying meaning of the source text. Yet, researchers have hesitated to implement these models in real world scenarios because of their tendency to introduce inconsistent statements, i.e. statements that are not supported by the original source text, also referred to as hallucinations. For instance, one study reported that 30% of radiology summaries created using a Transformer neural network model contained a least one inconsistency making a standard transformer encoder-decoder model impractical for healthcare.

Thus, it is with respect to these considerations and others that the present invention has been made.

SUMMARY OF THE DESCRIPTION

In one embodiment, the hospital course records for a patient's hospital stay are processed to automatically generate a hospital course section of a discharge summary that contains three sections: a history of patient illness (HPI) section, a daily section, and a follow-up section. Each of the three sections are textual abstractive summaries of a larger volume of electronic medical records that are entered by medical personnel, typically in a hospital setting.

In certain embodiments, the invention provides a machine learning (ML) architecture that generates an abstractive summary of the hospital course section of a discharge summary that provides day-to-day information about a patient's hospital stay. This method includes the steps of selecting the most important notes of a patient record, summarizing one or more sentences from these notes; and then combining the sentences sequentially so that it creates a human-like fluent summary of the patient record. Essentially, this automates the summarization of a medical chart.

In certain embodiments, the architecture constrains beam search to only consider predicted clinical words that are present in the source text. This reduces the introduction of non-factual statements during the summarization process. As a first step, constrained beam search creates a medical dictionary of banned words. If the model reaches a state during beam search where the word is within the set of banned words, then it backtracks. If beam search is unable to predict an appropriate word that is not banned, it will not generate a summary at all. This approach yields acceptable accuracy and consistency in an automated abstractive summary and improves processing of electronic medical records to produce high-quality summaries for physicians and clinicians as a means to automate their manual workflow.

Embodiments include a method and a computer server for generating a summary of a hospital stay by a patient, including maintaining a database of electronic medical records (EMRs) where the EMRs include clinical notes pertaining to a patient during a time interval, identifying a set of significant physician notes for the time interval, generating a candidate set of summaries for each of the significant physician notes, for each significant physician note, analyzing the factuality of each of the candidate summaries and selecting the most factual summary, and generating a daily section for inclusion in a hospital course section of a discharge note that includes the selected factual summary for each of the significant physician notes.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description of the Preferred Embodiment, which is to be read in association with the accompanying drawings, wherein:

FIG. 1 is a streamlined example of a discharge summary.

Figure 2:
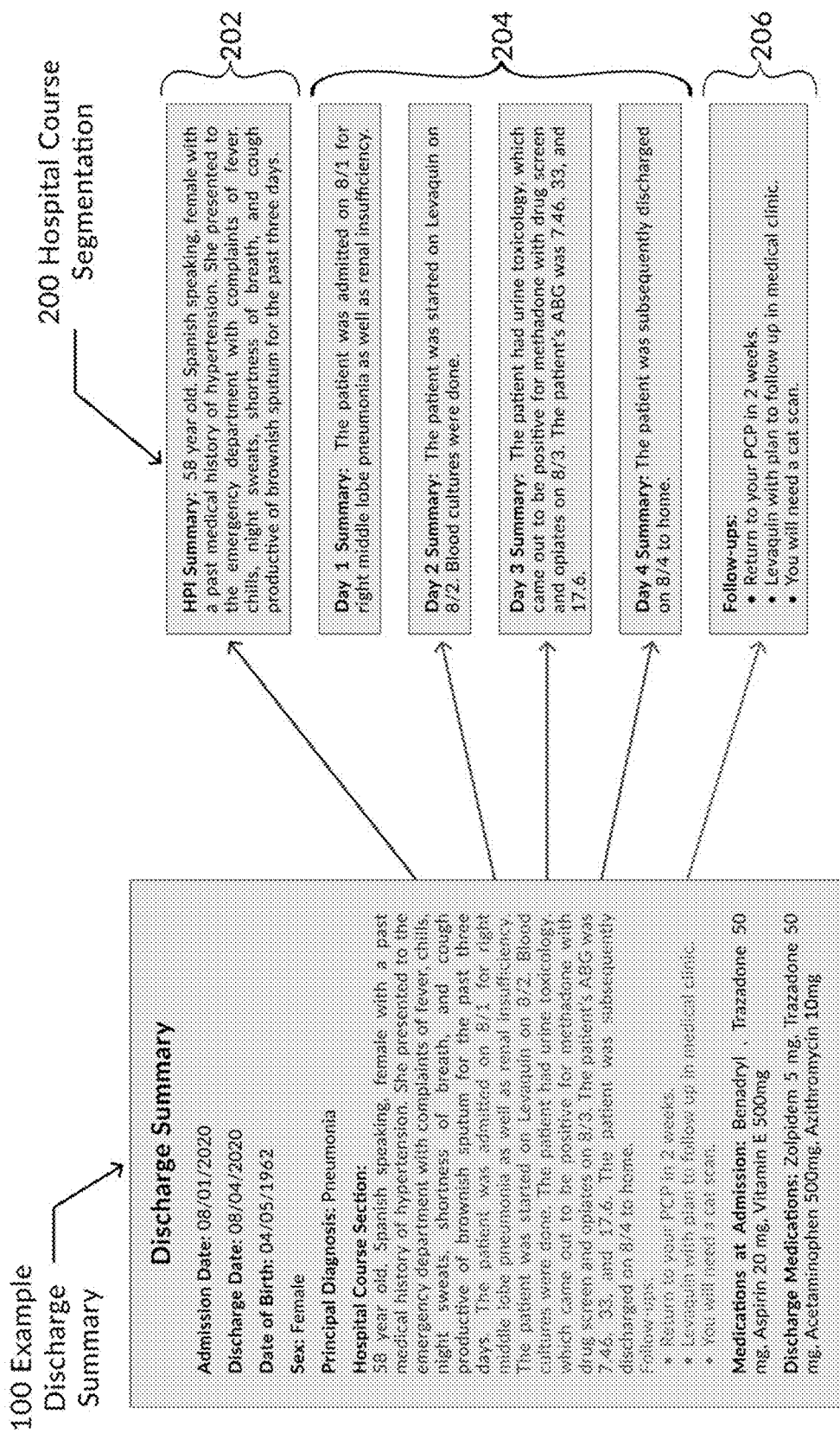
FIG. 2 illustrates the overall objective of the invention, which is to automatically extract summarized, accurate, textual data from specific fields of medical records.

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

The invention now will be described more fully hereinafter with reference to the accompanying drawings, which form a part hereof, and which show, by way of illustration, specific exemplary embodiments by which the invention may be practiced. This invention may, however, be embodied in many different forms and should not be construed as limited to the embodiments set forth herein; rather, these embodiments are provided so that this disclosure will be thorough and complete, and will fully convey the scope of the invention to those skilled in the art. Among other things, the invention may be embodied as methods, processes, systems, business methods or devices. Accordingly, the present invention may take the form of an entirely hardware embodiment, an entirely software embodiment or an embodiment combining software and hardware aspects. The following detailed description is, therefore, not to be taken in a limiting sense.

As used herein the following terms have the meanings given below:

Discharge Summary—refers to a document provided when a patient leaves a hospital that communicates the treatments provided during a hospital and recommends an outpatient care plan to the post-hospital care team. Often, the discharge summary is the only form of communication that accompanies the patient to the next setting of care. High-quality discharge summaries are generally thought to be essential for promoting patient safety during transitions between care settings, particularly during the initial post-hospital period.

Hospital Course Section—refers to a section in the discharge summary that describes the events occurring to a patient during a hospital stay, typically including a description of surgical, medical, specialty or allied health consults a patient experienced as an inpatient, and a description of any surgical, diagnostic, or other procedures performed on the patient. The term hospital course section, as used herein, refers to a collection of descriptions of daily events and procedures that pertain to an inpatient's hospital stay.

Clinical notes—refers to all notes in a medical record. The notes provide information about a patient and are typically in text, i.e. unstructured, format. There are many different types of clinical notes, including: Progress Note, Admit Note, Discharge Note, History & Physical Note, and Consult Note.

Physician—refers to a person in healthcare that has either a doctor of medicine (MD) or a doctor of osteopathic medicine (D.O.).

Clinician or provider—refers broadly to all types of healthcare providers who provide direct care for a patient, including inter alia a physician, nurse, psychologist, case managers. Generally, a clinician is the user of the subject invention and prepares, reads or otherwise uses or interacts with clinical notes.

Progress Note—refers to Clinical Note that provide medical details for each day of a patient's hospital stay about what happened to the patient that day. Progress information may be included in a number of types of clinical notes. Typically, the Progress Note is in the general format of SOAP (subjective, objective, assessment, and plan). So, physicians document what the patient told them (subjective), what data they get from examination such as labs and vitals (objective), what the physician's conclusion is about the data such as their diagnosis (assessment), and based on that conclusion, what sort of treatment should the patient undergo after discharge (plan).

Figure 4:
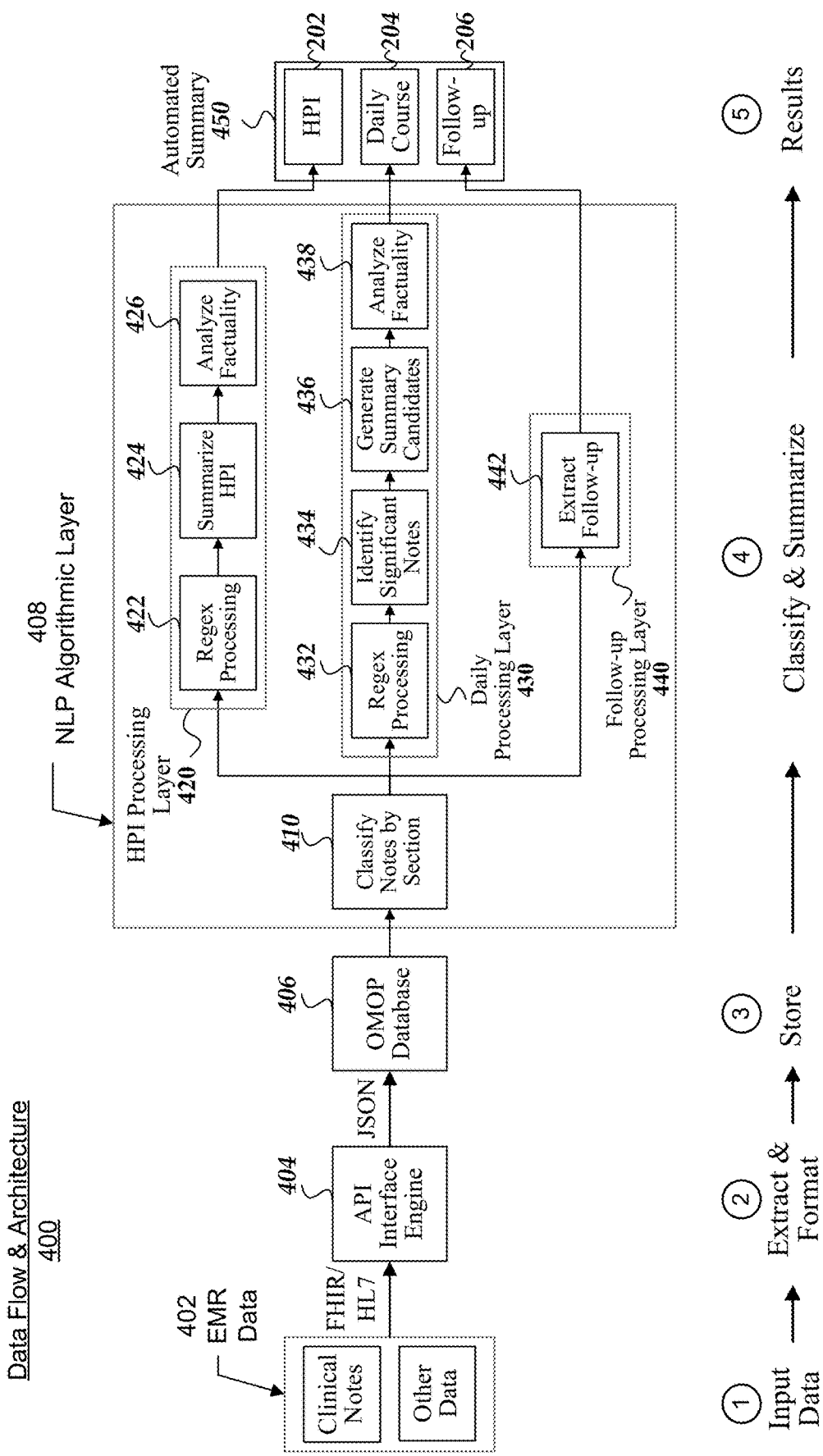
FIG. 4 illustrates an embodiment of a medical record data flow and processing architecture, referred to as MRAS architecture, that includes machine learning (ML) processing components.

Machine learning (ML) model or model—refers to a machine learning algorithm or collection of algorithms that takes structured and/or unstructured data inputs and generates a prediction or result. The prediction is typically a value or set of values. A ML model may itself include one or more component models that interact to yield a result. As used herein, unless otherwise stated a ML model refers to a neural network that receives text as input data and generates estimates or predictions relative to a known validation data set. Typically, the model is trained through successive executions of the model. A trained model represents a learned process for prediction. Typically, a model is executed successively during a training phase and after is has been successfully trained, is used operationally to evaluate new data and make predictions. It must be emphasized that the training phase may be executed 1000s of times in order to obtain an acceptable model capable of predicting success metrics. A transformer, described further hereinbelow, is a type of machine learning model that uses the algorithm of self-attention. In certain embodiments, The machine learning models used in steps 424, 434, 436, and 442 of FIG. 4 are all encode-decoder transformer models. In other embodiments, other machine learning models may be used for one or more of these steps.

Prediction—refers herein to a statistical estimate, or estimated probability, that measures how well either narrative text belongs to a specific class, a category of classes, or is an estimate of the precision and recall of a computer-generated text against a reference text, such as for comparing summaries. A prediction may also refer to an estimate or probability assigned to each class or category within a classification system that includes many individual classes.

Architecture—as used herein, refers to an overall set of methods stages, processing layers, procedures, or processes performed successively that transforms input or source data into output or results data. The architecture used in the present invention is described hereinbelow with reference to FIG. 4.

Generalized Operation

The operation of certain aspects of the invention is described below with respect to FIGS. 2-5.

FIG. 2 illustrates the overall objective of the invention, which is to automatically abstract summarized, accurate, textual data from specific fields of medical records and combine the content to produce a narrative summary. In one embodiment, the hospital course records for a patient's hospital stay are processed to automatically generate a hospital course section of a discharge plan summary 200, which contains three sections. The three sections are a history of patient illness (HPI) section 202, a daily section 204, and a follow-up section 206. Each of the three sections are textual abstractive summaries of a larger volume of electronic medical records that are entered by medical personnel, typically in a hospital setting.

History of present illness section 202 takes as input information such as an admission note, history and physical (H&P) notes, emergency department (ED) note, age, ethnicity, admission date and time, and an admission diagnosis.

Daily section 204 takes as input progress notes from a doctor or other medical personnel which are typically incorporated into the hospital course section of a discharge summary and includes information about procedures performed, consults, age, admission diagnosis and patient complaints.

Follow-up section 206 takes as input case management data, social worker notes, progress notes from a doctor or other medical personnel, a death note, discharge date and time and discharge disposition.

Figure 3:
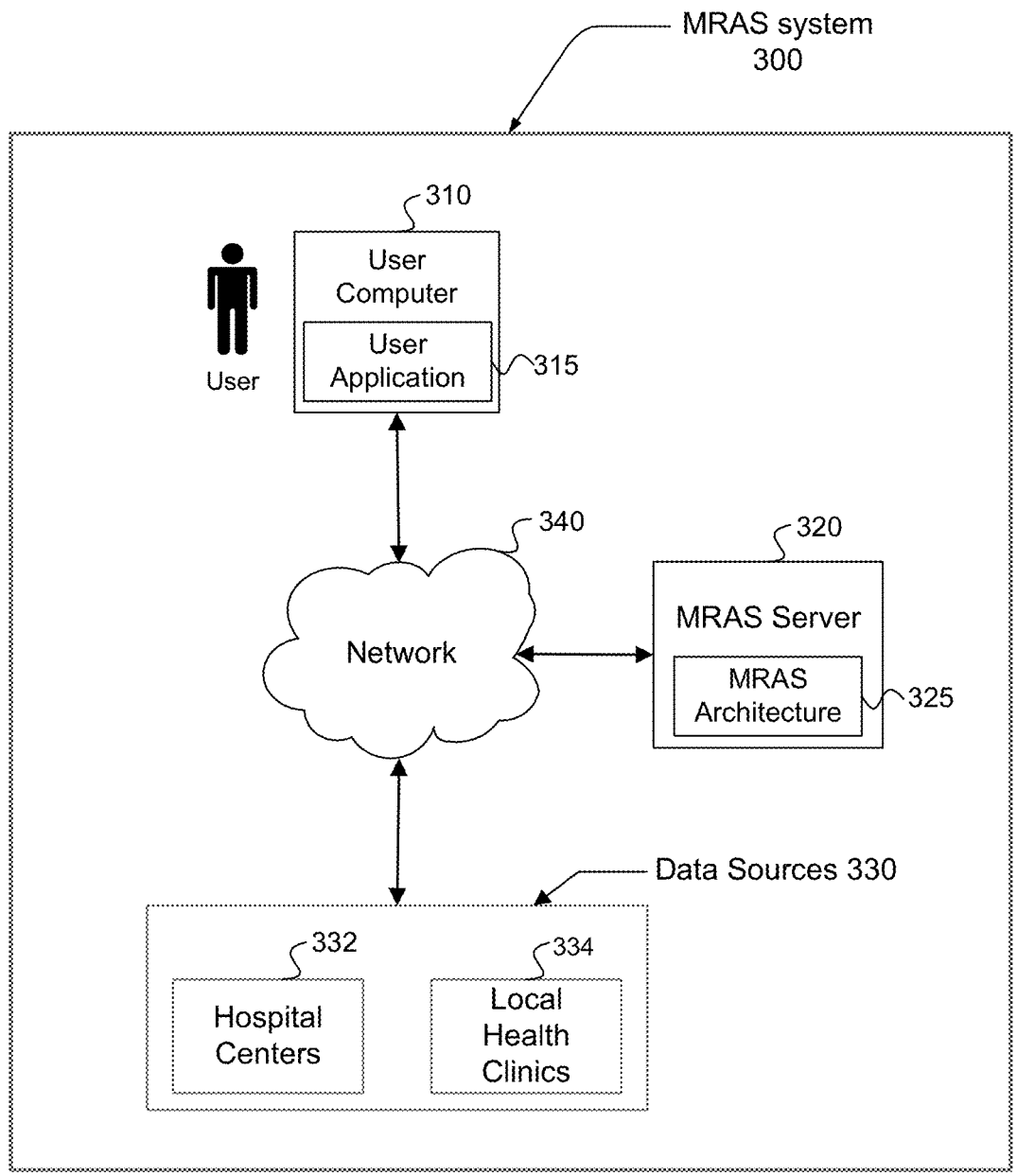
FIG. 3 illustrates one embodiment of a medical record abstractive summarization (MRAS) system.

FIG. 3 illustrates one embodiment of a medical record abstractive summarization (MRAS) system 300.

MRAS server 320 accesses data sources 330 which provide medical record data for analysis. The medical record data may be used during training of the model or may be live input data, used operationally for analysis and classification.

It may be appreciated that the medical records data used as input may come from a variety of sources. Some of the data may be in standardized formats and other may be in proprietary formats. The most substantial source of medical record data is data from hospital centers 332 and local health clinics 334, as described hereinbelow. However, other sources of data may be included without departing from the scope and spirit of the present invention.

Hospital centers 332 utilize staff who generate medical record data such as a hospitalist that completes a discharge order and discharge summary, a pharmacist who completes a medical reconciliation, a discharge planner and a transitional care nurse. The term hospital center is used to refer to the medical facility where a surgery or other patient treatment is performed. For example, in the case of an outpatient procedure the term hospital center may refer to a doctor's office or local health clinic.

Local health clinics 334, such as a county health clinic or private health clinic have staff that provide outpatient services and generate medical records as a consequence of providing these services. Such staff may include a primary care provider (PCP) team, a primary care provider that receives and reviews a discharge summary and completes records of follow-up appointments, a pharmacist, a care management team and an outreach worker such as a social worker or home care nurse or assistant.

Typically, MRAS server 320 accesses medical record data from data sources 330 across a network 340, although, in certain embodiments, medical record data may be provided on physical media like USB drives, hard drives and across other electronic communications media such as direct links. MRAS server 320 includes a processor, data storage for storing video clips and intermediate results, and a nonvolatile memory for storing program code and data.

MRAS server 320 may be implemented by a single server computer, by multiple server computers acting cooperatively or by a network service, or "cloud" service provided by a cloud service provider such as AMAZON AWS. Devices that may operate as MRAS server 320 include, but are not limited to personal computers, desktop computers, multiprocessor systems, microprocessor-based or programmable consumer electronics, network PCs, servers, network appliances, and the like.

A user interacts with MRAS server 320 to identify and provide training videos and clips to train supervised machine learning algorithm that are included in MRAS architecture 325. Typically, a user interacts with a user application 315 executing on user computer 310. User application 315 may be a native application or a web application that runs inside a web browser such as FIREFOX from MOZILLA, or CHROME from GOOGLE INC.

User computer 310 may be a laptop computer, a desktop personal computer, a mobile device such as a smartphone or any other computer that runs programs that can interact over network 340 to access MRAS server 320. Generally, user computer 310 may be a smart phone, personal computer, laptop computer, tablet computer, or other computer system with a processor and nontransitory memory for storing program instructions and data, a display and an interaction apparatus such as a keyboard and mouse.

MRAS server 320 typically stores data and executes MRAS architecture 325 described hereinbelow with reference to FIG. 4.

Network 340 enables user computer 310 and MRAS server 320 to exchange data and messages. Network 340 may include the Internet in addition to local area networks (LANs), wide area networks (WANs), direct connections, and combinations thereof.

Architecture and Data Flow

FIG. 4 illustrates an embodiment of a medical record data flow and processing architecture, referred to as MRAS architecture 400, that includes machine learning processing components and models. MRAS architecture 400 is an embodiment of MRAS architecture 325.

Generally, MRAS architecture 400 can be grouped into five overall components, which are (1) input data, (2) data extraction and formatting, (3) storage, (4) standardization and summarization, and (5) results. Each of the five components is discussed hereinbelow.

It may be appreciated the each of boxes in FIG. 4 may represent steps in an overall method, procedures that are performed entirely in software or hardware or by a combination of hardware.

1. Input Data

EMR data 402 represents, in the context of architecture 400, the repository or repositories of data that are accessed. EMR Data 402 is typically retrieved from a patient's medical record, which is maintained in one or more specialized computer systems such as an Electronic Medical Record (EMR) systems. EMR data 402 for a patient may include a wide range of data or document types, including clinical notes, and other data, including inter alia labs, vitals, and demographic information.

Clinical notes, as defined hereinabove, for a patient are the primary source of data for constructing the narrative summary of the course of treatment for the patient, referred to as a daily course. Clinical notes can be accessed in the EMR system in either the format of text, audio, or video. If the clinical notes are in the format of audio or video, additional processing steps may be taken to convert the audio or video into a textual format.

EMR data 402 typically includes both structured and unstructured data from the patient. Structured data is defined as data that is organized, categorical, and formatted for search within a database, while unstructured data, typically in the form of text, is not. Examples of unstructured data include text files, audio, videos, and images.

2. Extract & Format

EMR data 402 is retrieved by an API interface engine 404 through an API layer. An international standard, HL7, for exchanging data from one healthcare entity to another is used in certain embodiments. Use of HL7 facilitates transfer of data between the multiple different entities, enabling all parties to format and parse the data. FHIR is a recent version of the HL7 standard that is implemented with a RESTful web service and data formats such as XML and JSON. API interface engine 404 is designed to receive messages from the healthcare entity and translate the messages into a known format.

3. Store

Once the incoming data is properly formatted in the interface engine, it is stored in a database referred to as OMOP database 406. The data is stored using the Observation Medical Outcomes Partnership (OMOP) Common Data Model (CDM) which is a standardized format for medical terminologies. A benefit of OMOP is the ability to store clinical notes from different sources and link them to the proper patients and visits. Additionally, OMOP has a data structure that extends integration with insights gained from machine learning tools such as natural language processing (NLP).

4. Classify and Summarize

With the data properly stored in OMOP database 406, it may be transmitted to or received by an NLP algorithm layer 408. The NLP algorithm layer 408 constructs the narrative summary by first filtering the data through three processing pipelines, referred to as processing layers herein, as follows: history of present illness (HPI) processing layer 420, a daily processing layer 430, and follow-up processing layer 440.

Each processing layer includes a summarization step, specifically steps 424, 436 and 442, that summarizes or extracts the most important sentences or phrases from clinical notes. Thus far, the most successful machine learning model, in terms of generating accurate results, used for purposes of extraction and summarization of text is a transformer model. A transformer model is a neural network that learns context and thus meaning by tracking relationships in sequential data such as words in a sentence. First described in a 2017 paper from Google, "Attention Is All You Need" by Ashish Vaswani et al. [Vaswani], which is hereby incorporated by reference in its entirety, transformers have been widely used for processing text and speech. So, while other types of machine learning models can be used, and the invention is not restricted to the use of neural networks or transformer models, use of the transformer model will be assumed for subsequent discussion. More specifically, in the embodiment of the subject invention described herein steps 424, 434, 436, and 442 are implemented using transformer models. In each case, different combinations of data sets used to train the models are used, as discussed hereinbelow with reference to FIGS. 5A, 5B, 5C.

By way of background, two types of text summarization are commonly employed: extractive and abstractive. Extractive summarization identifies key terms and phrases from a text document and concatenates them to form a summary. Abstractive summarization generates new sentences through synthesis to form the summary. Transformer technology, with its sequence-to-sequence neural network architecture has improved the precision and accuracy of abstractive summarization to the point where it can be effectively used to generate an abstractive summary from a clinical note.

As previously discussed, while transformer models have proved successful for abstractive text summarization, summaries generated by transformer models often produce inconsistencies, i.e. statements not supported in the original source clinical notes at an unacceptable rate. To remedy this deficiency, the potential or candidate summaries generated by transformer models at steps 424, and 436 are subjected to an additional processing step that eliminates non-factual words or phrases.

In one embodiment, a novel algorithm, referred to herein as constrained beam search, analyzes summaries for factuality. Constrained beam search eliminates from summaries any words or phrases that are not present in the original source documents. This effectively reduces the likelihood that extraneous, non-factual statements, which have no basis in the source text of a corpus of clinical notes will be introduced into a resulting summary. An embodiment of an algorithm that performs constrained beam search is described in further detail with reference to Listing 1, hereinbelow.

While constrained beam search has been shown to provide excellent results for factuality analysis, the invention is not limited to this method of factuality analysis. However, other approaches may be used without departing from the scope of the subject invention. For example, a reinforcement learning approach can be used where a reward function is trained to improve an agent based on factuality.

Day-to-Day Processing

Since the basic time interval is one day, incoming clinical notes that related to a patient's hospital stay are processed on a day-to-day basis, with the object to provide an updated hospital course section of the discharge summary daily for each patient, or for selected patients. In certain embodiments, NLP algorithmic layer 408 first segments incoming notes into three sections and processes them accordingly on a daily basis.

At step 410, clinical notes and data from database 406 are classified into one of these three pipelines or processing layers, an HPI processing layer 420, a daily processing layer 430 and a follow-up processing layer 440. The classification algorithm performed by section classifier 410 may be as simple as a rule-based approach that looks at the categorical values of the type of data or it may a more robust approach such as a machine learning model that classifies data based on previous performance. In one embodiment, a rule-based approach that assigns documents to a processing layer based on both the type of clinician that authored a clinical note and the type of note is used. The clinical note author may be, for example, a MD, RN, NP. And common clinician note types, as previously discussed, include Admission Note, History & Physical Note, and Progress Note.

Further, in other embodiments, NLP algorithmic layer may process only a single section, e.g. daily processing layer 430. In this case, specific types of clinical notes, as required for a particular section, may be retrieved and step 410 may be omitted.

HPI Section Processing

For HPI processing layer 420, the primary data source is the Admission Note which can be named differently at healthcare institutions, for example it may be referred to as a History & Physical (H&P) note or an Emergency Department (ED) note, as determined by policies and regulations established by the medical provider. Accordingly, section classifier 410 classifies based on a set of rules based on specific note type and medical provider.

At step 422 a regular expression, or regex, processing algorithm is performed on the clinical notes to extract the most salient and useful content. Regexes use pattern matching rules to match and format data. By passing the clinical note through a series of regexes, it reduces the overall content passed to the next processing step. Specifically, at step 422 a regex processing algorithm filters incoming clinical notes to remove unnecessary information so the machine learning model, executed in the next step, does not get overburdened by too much data. For example, physicians often include sentences like "I confirm that this medical note accurately reflects all work, treatment, procedures, and medical decision making performed by me" in a clinical note; such statements may be included for legal or billing purposes but don't provide any useful clinical insights for the model. A regex can pattern match on such sentences to remove them before prior to execution of a ML model such as that which is executed at step 424.

Theoretically, all data can be passed to step 424 without performing step 422 since the machine learning model implemented at step 424 would identify the most salient content; however, in practice regexes significantly reduce processing time. Once the clinical notes have undergone regex processing, related structured data, such as the admission diagnosis, patient age, note date and time, is appended to the textual portion of the clinical note. For example, if an original clinical note states: "Patient is a 47 year old white male with a history of epilepsy who presents to Weill Cornell Medicine.", then structured data may be added at the beginning of the note to help with processing. Continuing the example, the edited note may read: "Admit Diagnosis: Epilepsy; Age: 47; Note Date: Jul. 21, 2022, Note Text: Patient is a 47 year old white male with a history of epilepsy who presents to Weill Cornell Medicine . . . ". This step enables, the machine learning model, which executes at step 426 to process the unstructured data.

Once preprocessed at step 422, the text is input as the source content to a transformer model at step 424 to generate a table or matrix that includes potential summaries, each assigned a probability. Each potential, summary generated at step 424 consists of a few predicted sentences that make up the first portion of the resulting Hospital Course Section of the Discharge Summary as illustrated in section 202 of FIG. 2. The transformer model employed at this step is pre-trained on the BART-CNN/Dailymail dataset and fine-tuned using a dataset constructed using data from the hospital course section of the discharge summary, prior to its use in inference, i.e. prior to operational use, as discussed hereinbelow with reference to FIG. 5A.

At step 426 factuality analysis is performed to eliminate non-factual words or phrases from the summary. As previously discussed, in one embodiment a constrained beam search algorithm, which is further described with reference to Listing 1, is used. In effect, the constrained beach search algorithm selects the best summary from those generated in the preceding step.

Daily Section

Daily processing layer 430 summarizes all significant clinical notes relative to a patient's hospital stay and abstracts the salient content from each of these notes. Daily processing layer 430 generates one or more sentences for each consecutive time interval, typically a day, for the duration of a patient's hospital stay, as illustrated in section 204 of FIG. 2. When combined together, these daily summaries create a complete narrative of a patient's daily events and status from admission to discharge.

For the Daily processing layer 430, the primary data source selected for use by section classifier 410 are physician notes provided by physicians that describe what is happening or recently happened to a patient; often they are related to a recent treatment event. Physician notes may include Progress Notes, Procedure Notes, Op Notes, or Consult Notes. Other types of data may also be included, but an overall effort is made to filter the source data based on the perceived clinical importance of the data to find the relevant interval history (what happened to the patient during a specified time frame such as one day). Note, that while the interval used herein is the day, hence the term Daily section, a shorter or longer interval may also be employed.

Two examples of sentences abstracted from physician notes that might be included in a daily narrative section are given below:

Example 1: On 12-22 coumadin was adjusted to previous dose of 1 mg daily.

Example 2: On the evening of 11-19, the patient was in Afib with RVR.

At step 432 each filtered clinical note resulting from step 410 is pre-processed using regex processing, as previously discussed with reference to step 422, to improve performance of the machine learning model that executes in the next step.

At step 434, the clinically significant notes are identified. Those deemed to be of lesser importance are discarded, i.e. they are not included in subsequent processing steps. The objective of this step is to decide, on a note-by-note basis, which clinical notes are important enough to summarize in order to keep the patient hospital summary generated by daily processing layer 430 concise; otherwise, if all relevant clinical notes were summarized the summary might contain hundreds or even thousands of sentences, depending on the length of the patient's hospital stay. Generally, for purposes of readability, a patient summary with at most 30-50 sentences is considered desirable.

In one embodiment, step 434 classifies each clinical note as to whether it is significant using a BERT transformer model, fine-tuned with a custom-created training dataset of clinical notes from the Daily section. The fine-tuning is described hereinbelow with reference to FIG. 5B. A different approach may also be used at this step, such as a rule-based approach. This step typically generates a list of documents to be summarized, or not, in the following step. There may be probabilities or confidence scores assigned to each document, or there may simply be a binary value that indicates whether or not the document is to be summarized for inclusion in the daily course summary.

At step 436 the clinical notes selected for further processing at step 434 are passed through a fine-tuned transformer model that generates a matrix, or ranked list of candidate abstractive summaries. Each summary includes one or more sentences. These constitute an abstractively generated summary of the hospital course section of the clinician note. In one embodiment, each candidate summary is limited to one or two sentences. Thus, the result from executing step 436 is a matrix or list of summaries for each clinician note deemed significant for the time interval being evaluated.

In one embodiment, summarization performed at step 436 uses a fine-tuned BART transformer as discussed hereinbelow with reference to FIG. 5C.

At step 438 factuality analysis is performed to eliminate non-factual words or phrases from the summary generated in the preceding step. As previously discussed, in one embodiment a constrained beam search algorithm, which is further described with reference to Listing 1, is used. In effect, the constrained beach search algorithm selects the best summary from those generated in the preceding step.

Follow-Up Processing

Follow-up processing layer 440 identifies any clinical content from the patient visit that needs to be acted upon by downstream clinicians after the patient is discharged from the hospital. The primary data source for follow-up processing layer 440, is hospital discharge planning information, which includes any information about what will happen to the patient after discharge. Discharge planning information is captured across a number of different clinical notes, i.e. it is not exclusive to or contained within any one type of note. Clinical notes that typically include hospital discharge planning information include case management notes, social work notes, and progress notes made prior to patient discharge, and death notes.

Includes one to two sentences from each clinical note that contains information about either discharge plans for a patient or expiration of the patient. Discharge plans primarily consist of stating post-discharge instructions for the patient so downstream providers can follow-up with the patient to ensure compliance and monitor their treatment. Examples of statements that might be abstracted from discharge plans for inclusion the follow-up section are given below:

Example 3: She was discharged in stable condition to home with home oxygen as she had ambulatory desats to 87%.

Example 4: Due to possible ligamentous injury, he will wear a soft cervical collar for four weeks; he will follow-up in the trauma clinic if his pain persists beyond four weeks.

From step 410, any relevant clinical notes that cover discharge planning are selected. Then, at step 442 every sentence is parsed using a natural language toolkit, NLTK, used to build Python language programs that work with human language. NLTK is an open-source toolkit, available from NTLK.org. And each of these sentences are then classified, again using a transformer model, as to whether they will be passed along to step 450 for inclusion in the results. If a sentence is classified as unimportant no further processing is performed.

Step 442, then, extracts follow-up sentences to be included in follow-up section 206. In one embodiment, a pre-trained BERT transformer model is used at this step for text classification. The result of step 442 is a list of extracted follow-up sentences. Other types of text classification methods may be used at this step including regression, logistic regression, random forest, or other machine learning models.

Results Processing

Lastly, step 450 takes the results from steps 424, 436, and 442 and sequentially compiles or generates an automated summary, intended for inclusion in a discharge summary that is automatically generated at the conclusion of a patient's hospital stay. The three sections addressed herein, namely HPI section 202, daily course section 204 and follow-up section 206, when taken together form an automated narrative summary of a patient's hospital stay. In certain embodiments, each of the three sections are generated automatically using abstractive summary technology that generates consists of a sequence of predicted sentences. In one embodiment, the HPI section 202 and daily course section 204 are abstractively summarized while follow-up section 206 is generated using extractive summarization. Additionally, at step 450 the sentences may be passed through a duplicate algorithm to remove any repeated sentences. The automated summary produced at step 450 is typically referred to as a Hospital Course Section.

As the hospital course section is constructed by sequentially combining sentences extracted from a sequence of time intervals, it can be produced prior to or after discharge as a tool for clinicians to quickly understand the most up-to-date information. When the automated summary is run while the patient is undergoing hospital discharge or after the patent is discharged it can serve as the Hospital Course section of the Discharge Summary.

Training the Model

Generally, supervised machine learning models are used to implement many of the processing steps in architecture 400. Here, the term supervised means that the model is trained using one or more training sets before the model is used operationally to predict results of live data.

Figure 5A:
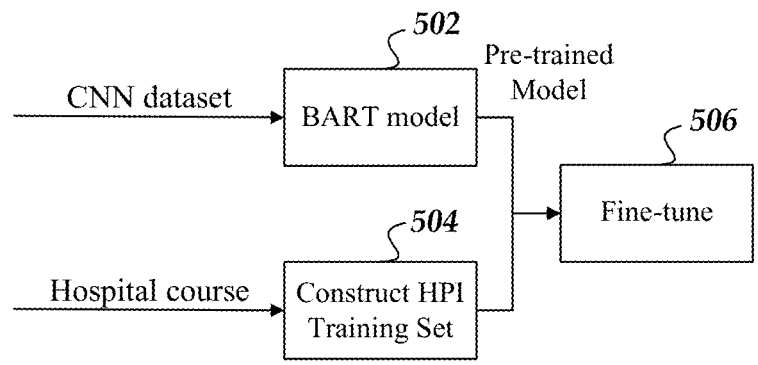
FIGS. 5A, 5B, 5C each illustrate embodiments of training methods used for supervised learning of the transformer models used in a natural language processing (NLP) algorithmic layer.
Figure 5B:
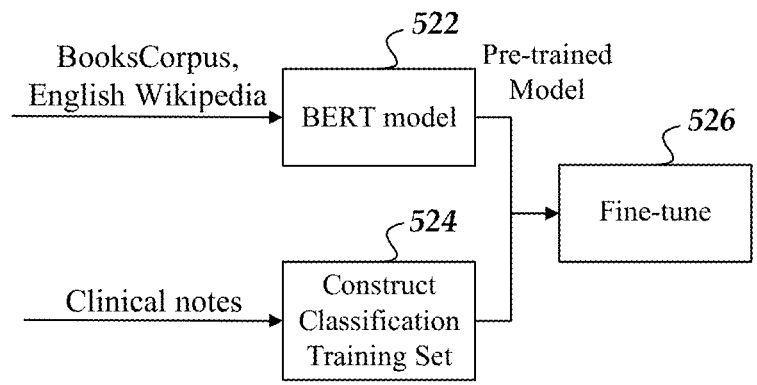
Figure 5C:
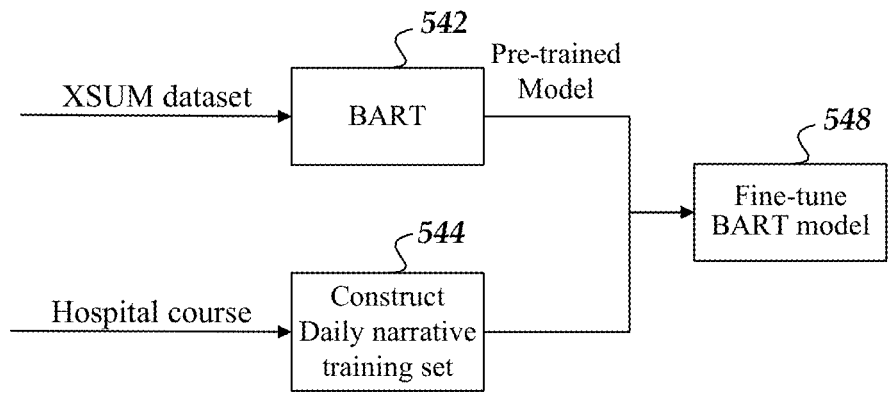

FIGS. 5A, 5B, 5C each illustrate the processing steps required to train the models used in each of the three sections: HPI, daily, and follow-ups. Although a variety of neural networks may be used, the best results have been obtained using transformer models; thus, the discussion below focuses on transformer embodiments.

The specific type of transformer model employed is an encoder-decoder transformer model designed for document summarization. The encoder-decoder structure as used in transformer models was introduced in [VASWANI]. The transformer model is first pre-trained on a large data set to learn language and the general task of document summarization. In embodiments described herein, pre-trained encoder-decoder transformers are selected from a Python library of 'transformers' available from Hugging Face. Hugging Face is a data science platform that provides tools that enable users to build, train and deploy machine learning (ML) models based on open source (OS) code and technologies. ML Models provided by organizations such as Hugging Face, Google and Microsoft are typically pre-trained on a particular dataset to provide certain capabilities. Some examples of pre-trained models that are designed for document summarization and which may be used include RoBERTA, BART, Pegasus, and T5.

Datasets which may be used for pre-training include CNN-dailymail, XSum, MIMIC-III, and PubMed. The choice of the pretrained model will determine how extractive or abstractive the performance of the predicted sentence. For example, the XSUM (Extreme Summarization) dataset for evaluation of abstractive single-document summarization systems; its goal is to create a short, one-sentence new summary answering the question "What is the article about?". while the CNN-Daily Mail dataset is more extractive and is used for English language text summarization.

HPI Training

At step 502 a BART transformer model is pre-trained using the CNN/Daily Mail training set. This results in a pre-trained BART model; that is specifically pre-trained to summarize documents written in the English language.

At step 504 a custom HPI training dataset is constructed. The HPI training dataset is constructed from the Hospital Course section of the Discharge Summary for a sizeable number of patient records. The first few sentences of each hospital course section is used as the label, i.e. the result or target on which the model trains.

At step 506 The pre-trained model is then further trained on the custom HPI training dataset, a process referred to as fine-tuning. In one test, the model was fine-tuned for 3 epochs with a batch size of 4. This fine-tuned transformer for the task of HPI sentence summarization is then used at the time of inference when new source documents are provided as input.

At step 508 a module is implemented to constrain the process of beam-search during inference to improve factuality for medical terminology. Beam search is the preferred inference method for transformer models that considers multiple alternative tokens based on a beam width and the predicted likelihood of each token. Abstractive encoder-decoder models, such as BART XSUM, have a tendency to hallucinate, i.e. to generate non-factual results. In the clinical domain, hallucinations, i.e. non-factual or inconsistent statements, not supported by the underlying source text are particularly problematic. Thus, a strategy of constraining beam search to control hallucination is deployed. The constrained beam search approach differs from regular beam search in that a set of banned words W will penalize a beam if selected and force it to backtrack. If a word is not selected from this set W, then the method functions as standard beam search.

The set of banned words W is constructed from a list of medical words maintained by SNOMED International, referred to SNOMED CT, by removing any words that appear in a source document. Other strategies may be deployed, such as altering the encoder-decoder model and adding a reinforcement learning approach to teach the model factuality. Lastly, before loading into the transformer model, the words within the source text are translated into integers through a pre-defined tokenizer.

Daily Section Training

Fine tuning of the transformer model used for document classification at step 434 is described hereinbelow with reference to FIG. 5B. First, at step 522 a BERT transformer model is pre-trained using BooksCorpus and English Wikipedia datasets. At step 524 a classification training dataset based on the clinical notes from the Daily Course section is created. Since the function of step 434 is to determine which clinical notes are considered clinically significant and therefore should be included in the hospital course summary each clinical note in the training set is labeled with either a 1 or 0, where 1 indicates the clinical note should be included for summarization and a 0 is assigned for clinical notes deemed not important enough to include for summarization or further processing. At step 526 the pre-trained BERT model is fine-tuned using the classification training dataset.

Fine tuning of the transformer model used for summarization of the Daily Section, performed at step 436, is described hereinbelow in method 540 with reference to FIG. 5C. First, at step 542 a BART transformer model is pre-trained using the XSUM dataset.

Then, at step 544 a daily narrative training dataset is created that takes a few summary sentences as the label from the hospital course section across many patient records. To create the dataset, sentences from a hospital course section that include a date are extracted—see Examples 1 and 2 hereinabove that illustrate examples of sentences that include a date.

Finally, at step 546 the pre-trained BART model is fine-tuned using the daily narrative training dataset Follow-Up Training In this embodiment, the BERT classification model is pre-trained using the CLIP/MIMIC-III dataset for identification of clinical action items.

Next, a discharge plan dataset is created. In one embodiment, to create this dataset, hospital course sections are filtered for clinical notes dated within 2 days of discharge. These notes are further filtered to include at least one of the following discharge related words: discharge, transfer, death, deceased, died, follow-up, priest, or AMA. Then the pre-trained BART model is fine-tuned using the discharge plan dataset.

Constrained Beam Search

One of the key issues addressed by the subject invention is to improve consistency and accuracy of the abstractive summarizations of clinical notes generated for inclusion in the Hospital Course Section of the Discharge note. Large due to an unacceptable error rate, including the introduction of non-factual statements, i.e. hallucinations, automated methods such as machine learning have previously proven unacceptable. An addition, novel processing element, referred to herein as constrained beam search has been created specifically to improve natural language processing technology in the medical records area. Testing has thus far shown, that with this approach the subject invention improves consistency by an average of 35% under certain conditions.

Table 1, hereinbelow, gives an example of how constrained beam search can improve automated summarization of a clinical note. In this case, a source note T1 is an admission note written by a physician. A BART transformer model trained using a MIMIC-III dataset generates a first summary T2. T2 includes two elements, the phrase "altered mental status" and the word "hypotension" which are not accurate, and which use terminology not present in the admission note. A summary produced using a BART transformer model trained with the same dataset, MIMIC-III, but which is adapted to use the constrained beam search algorithm yields an improved, acceptable, summary T3, that eliminates the two errors.

Standard beam search is a commonly used inference method for transformer models. The inference method is the algorithm used as part of the last step to produce their final output. Another commonly used inference method, greedy search, would consider only the most likely output for each word in the text selection.

In contrast, standard beam search considers multiple alternatives based on the "beam width", i.e. the number of alternative output sequences that will be considered as each position in the sequence of words. Each generated token, i.e. potential sequence of output words, is saved as a candidate, and the top beam widths are saved after each time-step. Once the <end> token is predicted, the best beam is chosen as the output, where the final beam selected is taken as the text summary of the input text sequence.

The constrained beam search approach, as used herein, incorporates a set of banned words, $W_{banned}$, that penalize a beam if selected and force it to backtrack. Thus, if a particular beam includes a word from the banned word list $W_{banned}$, then a new beam is added as a candidate. If a beam does not include a word from W then the method functions as standard beam search.

In one embodiment a dictionary of 79,521 medical words from a standard list of terminology, SNOMED CT, is used to construct $W_{banned}$. SNOMED-CT is a standard for electronic exchange of clinical health information used by the U.S. Federal Government. It includes a comprehensive, multilingual health terminology. It is available from the National Library of Medicine.

In one embodiment, the terminology available for summarization is obtained by selecting words from SNOMED CT that are used in a selection of clinical notes. For example, in one embodiment of HPI processing layer 420 only technical words from SNOMED CT that are also present in an original Admission Note or History & Physical note are available for use in a summary.

A two-part algorithm for constructing and then using $W_{banned}$ for inference as part of the processing of a machine learning model, including encoder-decoder transformer models, is given in Listing 1.

Part A of the algorithm, given in Lines A1-A5, provide a method for constructing a banned word list $W_{banned}$. Lines A1-A3 first construct an approved list of word, which includes the intersection of words used in a standard terminology list, for example, SNOMED CT, and the words contained in all source documents, i.e. clinical notes, provided to the algorithm. Line A4 adds to the approved list all synonyms. Then at line A4 $W_{banned}$ is formed by eliminating all approved words from the standard terminology list.

The result of Part A is that words not used in the original source document or words that are not synonyms of such cannot be used to produce an abstractive summary. This effectively reduces the likelihood that extraneous, non-factual statements, which have no basis in the source text of a corpus of clinical notes will be introduced into a summary.

Part B of the algorithm, given in lines B1-610, provide a method for performing inference, i.e. generating an abstractive summary across a number of words, using the $W_{banned}$ list created in Part A.

At line B4 a standard beam search is performed across a number of consecutive words in a clinical summary. At line B5 if one of the words in a beam is an element of $W_{banned}$ then this beam is eliminated as a possible result. Upon conclusion of the algorithm, at step line B10, the beam or word sequence with the highest probability is returned as a result.

The above specification, examples, and data provide a complete description of the manufacture and use of the composition of the invention. Since many embodiments of the invention can be made without departing from the spirit and scope of the invention, the invention resides in the claims hereinafter appended.

TABLE 1

| Ref | Type of Model | Text |
|---|---|---|
| T1 | Admission Note - Source Text | . . . 55-year-old male with history of two vessel CAD, ischemic cardiomyopathy, EF 15%, mitral regurgitation, and diabetes on oral agents who presents from OSH s/p VT/VF cardiac arrest . . . |
| T2 | BART | 55-year-old male with history of two vessel CAD, ischemic cardiomyopathy EF 15%, now s/p VT/VF arrest with altered mental status and hypotension. |
| T3 | BART with Constrained Beam Search | 55-year-old male with history of two vessel CAD, ischemic cardiomyopathy EF 15%, now s/p VT/VF arrest with cardiogenic shock, and mitral regurgitation. |

Listing 1

```
Part A - Generate list of banned words W_banned
A1      V_M ← medical vocabulary
A2      x ← clinical note (*source document)
A3      x_M ← V_M ∩ x
A4      x_M ← x_M + GetSynonyms(x_M)
A5      W_banned ← V_M − x_M
Part B - Use W_banned to constrain Beam Search for inference
B1      y := {y_seq, y_score}
B2      for β in beam width do
B3          while y_βseq^−1 ≠ <end> do
```

-continued

Listing 1

```
B4          y_βseq^(i), y_βscore^(i) = BeamSearch(x, y_βseq)
B5          if y_βseq^(i) ∈ W_banned then
B6              return y_βscore := −∞
B7          end if
B8          end while
B9      end for
B10     return y_βseq such that max(y_score)
```

What is claimed is:

1. A computer-implemented method of using a transformer machine learning model to generate a summary of a hospital stay by a patient, comprising:
maintaining a database of electronic medical records (EMRs) for patients, the EMRs include clinical notes written by clinicians that provide details about patients' hospital stays, the clinical notes including physician notes provided by physicians;
training the transformer model on a classification training dataset based on a daily course section of the clinical notes;
selecting from the database physician notes for a patient's hospital stay during a designated time interval;
identifying from the selected physician notes a set of significant physician notes for the time interval;
generating a candidate set of summaries for each of the identified significant physician notes, wherein a summary includes one or more sentences that are abstractively generated using the transformer model;
for each significant physician note, performing a factuality analysis on the candidate summaries, wherein the factuality analysis (1) eliminates any summary that includes a non-factual medical word or phrase, and (2) selects the highest probability remaining summary; and
generating a daily section for inclusion in a hospital course section of a discharge note, the generated daily section including the selected factual summary for each of the significant physician notes.

2. The method of claim 1 further comprising:
retrieving electronic medical records for a patient;
translating the received medical records into a standard format; and
storing the translated medical records in the database.

3. The method of claim 1 wherein the time interval is a day.

4. The method of claim 1 further comprising:
performing a regular expression (regex) processing step on the selected physician notes to extract the most salient and useful content for further processing.

5. The method of claim 1 wherein the physician note is selected from the group consisting of Progress Notes, Procedure Notes, Op Notes, and Consult Notes.

6. The method of claim 1 wherein identifying a set of significant physician notes is performed using a machine learning model.

7. The method of claim 6 wherein the machine learning model is a transformer model and the transformer model is fine-tuned using a dataset comprising clinical notes.

8. The method of claim 1 wherein the transformer model is fine-tuned using a dataset comprising clinical notes.

9. The method of claim 8 wherein the dataset of clinical notes comprises:

a daily narrative training set that includes sentences from hospital course sections of clinical notes, and wherein the clinical notes contain a date that falls within the time interval; and a discharge plan training set that includes EMRs that include discharge related words.

10. The method of claim 1 wherein analyzing the factuality of each of the candidate summaries is performed by a constrained beam search algorithm.

11. The method of claim 10 wherein the constrained beam search algorithm comprises:

constructing a banned word list that specifies medical terms that cannot be included in the automatically generated summary;

eliminating any summary that includes a term included in the banned word list, and using a transformer model to compute and select the highest probability remaining candidate summary.

12. A server computer, comprising:

a processor, a communication interface in communication with the processor;

a data storage for storing a database of clinical notes, wherein a clinical note is written by a clinician and provides details about a patient's hospital stay, the clinical notes comprising physician notes provided by physicians; and a memory in communication with the processor for storing instructions, which when executed by the processor, cause the server:

to train a transformer model on a classification training dataset based on a daily course section of the clinical notes;

to select from the database physician notes for a patient's hospital stay during a designated time interval;

to identify from the physician notes a set of significant physician notes for the time interval;

to generate a candidate set of summaries for each of the identified significant physician notes, wherein a summary includes one or more sentences that are abstractively generated using the transformer model;

for each significant physician note, to perform a factuality analysis on the candidate summaries, wherein the factuality analysis (1) eliminates any summary that includes a non-factual medical word or phrase, and (2) selects the highest probability remaining summary; and to generate a daily section for inclusion in a hospital course section of a discharge note, the generated daily section including the selected factual summary for each of the significant physician notes.

13. The server computer of claim 12 wherein the instructions, when executed by the processor, further cause the server:

to retrieve electronic medical records for a patient;

to translate the received medical records into a standard format; and to store the translated medical records in the database.

14. The server computer of claim 12 wherein the time interval is a day.

15. The server computer of claim 12 wherein the instructions, when executed by the processor, further cause the server:

to perform a regular expression (regex) processing step on the selected physician notes to extract the most salient and useful content for further processing.

16. The server computer of claim 12 wherein the physician note is selected from the group consisting of Progress Notes, Procedure Notes, Op Notes, and Consult Notes.

17. The server computer of claim 12 wherein identifying a set of significant physician notes is performed using a machine learning model.

18. The server computer of claim 17 wherein the machine learning model is a transformer model and the transformer model is fine-tuned using a dataset comprising clinical notes.

19. The server computer of claim 12 wherein the transformer model is fine-tuned using a dataset comprising clinical notes.

20. The server computer of claim 19 wherein the dataset of clinical notes comprises:

a daily narrative training set that includes sentences from hospital course sections of clinical notes, and wherein the clinical notes contain a date that falls within the time interval; and a discharge plan training set that includes EMRs that include discharge related words.

21. The server computer of claim 12 wherein analyzing the factuality of each of the candidate summaries is performed by a constrained beam search algorithm.

22. The server computer of claim 21 wherein the constrained beam search algorithm comprises:

constructing a banned word list that specifies medical terms that cannot be included in the automatically generated summary;

eliminating any summary that includes a term included in the banned word list, and using a transformer model to compute and selecting the highest probability remaining candidate summary.

* * * * *